United States Patent [19]

Métivier et al.

[11] Patent Number: 5,049,676

[45] Date of Patent: Sep. 17, 1991

[54] PROCESS FOR THE PREPARATION OF OPTICAL ISOMERS OF 2-CHLOROPROPIONIC ACID ESTERS

[75] Inventors: Pascal Métivier, Lyons; Harivelo Rajoharisson, Echirolles, both of France

[73] Assignee: Rhone-Poulenc Chimie, Courbevoie, France

[21] Appl. No.: 530,180

[22] Filed: May 30, 1990

[30] Foreign Application Priority Data

May 30, 1989 [FR] France ................................ 89 07370

[51] Int. Cl.$^5$ .................. C07D 213/63; C07D 333/32; C07D 307/58; C07C 69/63
[52] U.S. Cl. ................................ 546/302; 546/296; 549/66; 549/478; 549/479; 560/226; 560/228; 560/229; 560/230
[58] Field of Search ............... 560/226, 229, 228, 230; 549/66, 479, 478; 546/296, 302

[56] References Cited

PUBLICATIONS

Buathier, et al, Chem. Abstracts, 95(1):168563w (1981).

Azzena et al, Chem. Abstracts, 112(19)178030d (1989).

Primary Examiner—Johann Richter

[57] ABSTRACT

A process for the preparation of optically active esters of 2-chloropropionic acid of the formula:

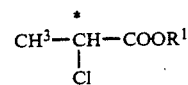

I from an optically active lactate of the formula:

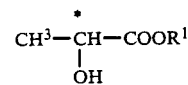

II with inversion of configuration. $COOR_1$ in formula I and formula II is a hydrolyzable group. The lactate of formula II is brought into contact with $SOCl_2$, followed by decomposition of the chlorosulfite formed, the process being one in which at least the decomposition stage is carried out in the presence of an ether.

12 Claims, No Drawings

PROCESS FOR THE PREPARATION OF OPTICAL ISOMERS OF 2-CHLOROPROPIONIC ACID ESTERS

The invention relates to a process for the preparation of optically active esters of 2-chloropropionic acid from the corresponding optically active lactic esters, with inversion of configuration, in the presence of thionyl chloride. The compounds prepared by the process of the invention are well-known chemical intermediates for obtaining chemical products which are particularly useful as herbicides. The advantage of preparing optically active herbicides lies in the fact that they are active in dosages which are smaller by one-half than the corresponding racemic compounds. This reduced dosage leads to a major advantage, especially insofar as preserving the environment is concerned.

Many processes have already been proposed in order to achieve this synthesis with the highest possible yields using thionyl chloride. Thus, French Patent FR-B-2,459,221 describes the chlorination of the racemic or optically active alkyl lactic ester in the presence of thionyl chloride and of an organic base while maintaining in the reaction mixture a molar excess of thionyl chloride of at least 2.5% relative to the quantity of alkyl lactate introduced into the mixture, at a temperature kept below the decomposition temperature of the alkyl lactate chlorosulfite during this first stage and then, in a second stage, heating the reaction mixture resulting from the first stage to a temperature which is at least equal to the decomposition temperature of the alkyl lactate chlorosulfite.

British Patent GB 2,055,802 describes the preparation of optically active esters of α-chloro- or α-bromopropionic acids which comprises the reaction of (L)-lactic acid ester with thionyl chloride or bromide a) in the presence of a base to give the ester of (D) α-chloro or bromopropionic acid with inversion of configuration or b) in the absence of a base to give an ester of (L)-α-chloro or bromopropionic acid with retention of configuration.

Furthermore, the reference: Cram and Hammond, "Organic Chemistry," McGraw-Hill, 1959, pages 236–239, teaches the reaction of optically active 2-octanol with SOCl$_2$ to give the 2-octyl chlorosulfite, which is then decomposed in dioxane to produce 2-chlorooctane with 68% retention of configuration and 32% of racemization.

It has now unexpectedly been found that it is possible to prepare the optically active 2-chloropropionate ester of the formula:

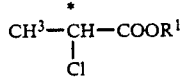

from an optically active lactate of the formula:

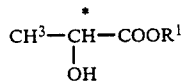

with inversion of configuration, by bringing the lactate of formula II into contact with SOCl$_2$ followed by decomposition of the chlorosulfite obtained, wherein at least the decomposition stage is carried out in the presence of an ether and wherein COOR$_1$ in formula I and formula II is a hydrolyzable group.

The group R$_1$ is preferably selected from the following radicals:

linear or branched C$_1$–C$_{18}$ alkyl, preferably C$_1$–C$_{12}$
linear or branched C$_2$–C$_{18}$ alkenyl, preferably C$_2$–C$_{12}$
linear or branched C$_2$–C$_{18}$ alkynyl, preferably C$_2$–C$_{12}$
linear or branched C$_3$–C$_{18}$ cycloalkyl, preferably C$_3$–C$_{12}$
C$_6$–C$_{14}$ aryl, preferably C$_6$–C$_{10}$, and
linear or branched C$_7$–C$_{15}$ aralkyl, preferably C$_7$–C$_{11}$.

These radicals may optionally be substituted by at least one substituent selected from one or more halogen atoms and C$_1$–C$_6$ alkoxy or alkylthio radicals. Furthermore, one to four carbon atoms of an aromatic ring of the aryl or aralkyl radicals set forth above may respectively be replaced by from one to four hetero atoms selected from oxygen, sulfur and nitrogen atoms. For example, furyl, thienyl (the radical of thiophene), and pyridyl radicals can be employed as R$^1$ radicals.

R$_1$ is preferably a C$_1$–C$_6$ alkyl radical.

Illustrative ethers include:

open-chain aliphatic ethers such as: ethyl vinyl ether, diethyl ether, sulfuric ether, 3-oxapentane, di-n-propyl ether, diisopropyl ether, butyl vinyl ether, butyl ethyl ether, di-n-amyl ether, 1-pentoxypentane, diisopentyl ether, diisoamyl ether, 1,2-dimethoxyethane, ethylene glycol dimethyl ether, and diethylene glycol dimethyl ether (diglyme);

aliphatic ethers with closed chains such as: ethyl oxide, propylene oxide, 2-methyloxacyclopropane, 1,2-epoxybutane 1,8-epoxy-p-menthane, 1,3,3-trimethyl-2-oxabicyclo[2.2.2]octane furan, furfuran, divinylene oxide, tetrahydrofuran, oxacyclopentane, p-dioxane, 1,4-dioxane, 1,3-dioxane, tetrahydropyran; and aromatic ethers like the following ethers: benzyl ethyl ether, α-ethoxytoluene methoxybenzene, ethoxybenzene, dibenzyl ether, diphenyl ether, and o-dimethoxybenzene.

The operation may preferably be carried out in two ways:

In the first method, it is possible to react the lactate of formula II directly with thionyl chloride in a first step to obtain the chlorosulfite

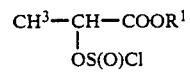

and then, in a second step, to decompose the chlorosulfite of formula III at an appropriate temperature in the presence of an ether.

In the first step, the molar ratio SOCl$_2$: lactate of formula II generally ranges from 0.8:1 to 2:1 and preferably is higher than 1.05:1. The temperature in the first step may vary from 0° C. to the boiling point of SOCl$_2$ and is preferably higher than 20° C.

Insofar as the second step of the first method is concerned, in general, without this constituting a critical feature, the dilution of the chlorosulfite relative to the ether is between 5 and 95% by weight of chlorosulfite compared to the weight of ether. The decomposition temperature is generally between 80° C. and the boiling temperature of the ether or lower than 140° C. if the ether has a higher boiling temperature.

In the second method, which is more preferred, the lactate of formula II, the thionyl chloride and the ether are brought into contact under the same conditions and in proportions which are identical with the preceding method of implementation, the chlorosulfite being replaced by the lactate for the dilution with the ether for the indications of proportions, namely: $SOCl_2:II$ on a molar basis generally ranging from 0.8:1 to 2:1, and preferably higher than 1.05:1, lactate:ether, dilution by weight of between 5% and 95%.

After mixing the three constituents, heating is applied at a temperature identical to that used in the second step of the first method. In other words, sufficient heat is applied to decompose the chlorosulfite. As stated above, the decomposition temperature is generally between 80° C. and the boiling temperature of the ether or lower than 140° C. if the ether has a higher boiling temperature.

EXAMPLE 1

Reactants

| | | | |
|---|---|---|---|
| D-Methyl lactate (96.7% as D enantiomer) | 5 ml | 5.45 g | 0.052 moles |
| $SOCl_2$ | | 9.3 g | 0.078 moles |
| diglyme dried over sieve | 15 ml | 14.09 g | |

Operating method

The diglyme and $SOCl_2$ were charged into a 50-ml three-necked flask under argon, fitted with a magnetic stirrer, a condenser and a thermometer. The lactate was run in over 35 min at room temperature and heating was carried out at 100° C. for 10 h.

The vapor phase chromatography (VPC) determination of the crude reaction product showed a degree of conversion of 62.3% and an actual determined chloropropionate yield of 43.2%.

The crude reaction product was taken up with 30 ml of $CH_2Cl_2$ and was then washed with $3 \times 15$ ml of water, was dried over $Na_2SO_4$, filtered and evaporated under vacuum. Chiral VPC analysis of this reaction mixture showed that the chloropropionate obtained contained 95.4% of the L enantiomer and 4.5% of the D enantiomer, which constituted an enantiomeric yield of 90%.

EXAMPLE 2

Reactants

| | | | |
|---|---|---|---|
| D-Methyl lactate (96.7% as D enantiomer) | 5 ml | 5.45 g | 0.052 moles |
| $SOCl_2$ | | 7.4 g | 0.062 moles |
| 1,4-dioxane (over sieve) | 15 ml | 15.9 g | |

Operating method

The dioxane was charged into a 50-ml three-necked flask fitted with a condenser, a thermometer and a magnetic stirrer. The $SOCl_2$ was run in gently (a slight exothermia was noted); once the temperature had returned to 25° C., the lactate was run in over 1 h. The reaction mixture was then heated to 100° C. for 26 h.

Determination of the crude reaction mixture using vapor phase chromatography showed a degree of conversion of 60.6% and an actual determined chloropropionate yield of 15.7%. A two-dimensional chromatography carried out on the crude reaction mixture showed that the chloropropionate obtained had an L isomer content of 82.4%, which constituted an enantiomeric yield of 65%.

We claim:

1. A process for the preparation of an optically active ester of 2-chloropropionic acid of the formula:

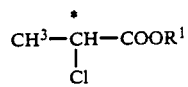

from an optically active lactate of the formula:

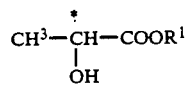

with inversion of configuration, comprising the steps of bringing the lactate of formula II into contact with $SOCl_2$ to obtain a chlorosulfite; and decomposing the chlorosulfite formed, wherein at least the decomposition step is carried out in the presence of an ether and wherein $COOR_1$ in formula I and formula II is a hydrolyzable group.

2. The process of claim 1, wherein the group $R_1$ is selected from the radicals:
linear or branched $C_1-C_{18}$ alkyl,
linear or branched $C_2-C_{18}$ alkenyl,
linear or branched $C_2-C_{18}$ alkynyl,
linear or branched $C_3-C_{18}$ cycloalkyl,
$C_5-C_{14}$ aryl, and
linear or branched $C_7-C_{15}$ aralkyl,
wherein said radical(s) may be optionally substituted by at least one substituent selected from one or more halogen atoms and $C_1-C_6$ alkoxy or alkylthio radicals, and further wherein one to four carbon atoms of an aromatic ring of said aryl or aralkyl radical(s) may be respectively replaced by from one to four hetero atoms selected from oxygen, sulfur and nitrogen atoms.

3. The process of claim 2 wherein said $R_1$ group is selected from the radicals:
linear or branched $C_1-C_{12}$ alkyl,
linear or branched $C_2-C_{12}$ alkenyl,
linear or branched $C_2-C_{12}$ alkynyl,
linear or branched $C_3-C_{12}$ cycloalkyl,
$C_6-C_{10}$ aryl, and
linear or branched $C_7-C_{11}$ aralkyl and further wherein one of four carbon atoms of an aromatic ring of said aryl radical may be replaced by from one to four hetero atoms to form a hetero radical selected from furyl, thienyl and pyridyl.

4. The process of claim 3, wherein $R_1$ is a $C_1-C_6$ alkyl radical.

5. The process of claim 1, wherein said ether is selected from diglyme and dioxane.

6. The process of claim 1, wherein the molar ratio of lactate of the formula II to $SOCl_2$ ranges from 0.8:1 to 2:1.

7. The process of claim 6, wherein said molar ratio ranges from higher than 1.05:1 to 2:1.

8. The process of claim 1, wherein the decomposition temperature ranges from 80° C. to the boiling temperature of the ether or is lower than 140° C. if the ether has a higher boiling temperature than 140° C.

9. The process of claim 1, wherein, in a first step, the lactate of formula II and thionyl chloride are brought into contact to obtain the chlorosulfite of the formula:

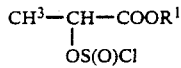

and the chlorosulfite of formula III is then decomposed in a second step in the presence of an ether.

10. The process of claim 9, wherein the dilution of the chlorosulfite relative to the ether ranges from 5 to 95% by weight of chlorosulfite compared to the weight of ether.

11. The process of claim 1, wherein the lactate of formula II, thionyl chloride and the ether are brought into contact and wherein heating is then carried out to decompose the chlorosulfite obtained.

12. The process of claim 11, wherein the dilution of the lactate relative to the ether ranges from 5 to 95% by weight of lactate compared to the weight of ether.

UNITED STATES PATENT AND TRADEMARK OFFICE
CERTIFICATE OF CORRECTION

PATENT NO. : 5,049,676
DATED : September 17, 1991
INVENTOR(S) : Pascal Metivier, et al.

It is certified that error appears in the above-identified patent and that said Letters Patent is hereby corrected as shown below:

Title page, item 75   change "Lyons" to --Lyon--.

Title page, column 2, line after "Primary Examiner - Johann Richter" insert --Attorney, Agent or Firm - Finnegan, Henderson, Farabow, Garrett & Dunner--.

Signed and Sealed this

Fourth Day of May, 1993

Attest:

MICHAEL K. KIRK

Attesting Officer       Acting Commissioner of Patents and Trademarks